United States Patent [19]

Richards et al.

[11] Patent Number: 5,273,041
[45] Date of Patent: Dec. 28, 1993

[54] FIBER OPTIC PHOTOPLETHYSMOGRAPH FOR A MAGNETIC RESONANCE IMAGING SYSTEM

[75] Inventors: Karl T. Richards; Randall H. Buchwald; Donald R. Jansta, all of Waukesha; Robert R. Lijewski, Milwaukee, all of Wis.

[73] Assignee: General Electric Company, Milwaukee, Wis.

[21] Appl. No.: 876,656

[22] Filed: Apr. 30, 1992

[51] Int. Cl.⁵ .............................. A61B 5/055
[52] U.S. Cl. .................. 128/653.2; 128/653.5; 128/666; 128/687
[58] Field of Search .............. 128/653.2, 653.5, 633, 128/666, 667, 687

[56] References Cited

U.S. PATENT DOCUMENTS

| | | | |
|---|---|---|---|
| 4,580,219 | 4/1986 | Pelc et al. | 364/414 |
| 4,602,641 | 7/1986 | Feinberg | 128/653.3 |
| 4,663,591 | 5/1987 | Pelc et al. | 324/309 |
| 4,685,464 | 8/1987 | Goldberger et al. | 128/633 |
| 4,694,837 | 9/1987 | Blakeley et al. | 128/653.2 |
| 4,706,026 | 11/1987 | Pelc et al. | 324/309 |
| 4,720,678 | 1/1988 | Glover et al. | 324/309 |
| 4,751,462 | 6/1988 | Glover et al. | 324/309 |
| 4,830,014 | 5/1989 | Goodman et al. | 128/666 |
| 4,840,179 | 6/1989 | Ullrich | 128/633 |
| 5,051,903 | 9/1991 | Pelc et al. | 364/413.13 |
| 5,074,309 | 12/1991 | Gerot | 128/687 |
| 5,111,817 | 5/1992 | Clark et al. | 128/666 |

OTHER PUBLICATIONS

Yoshiya et al, "Spectrophotometric Monitoring of Arterial Oxygen Saturation in the Fingertip", Med. & Biol. Eng. & Comp. Jan. 1980 pp.27-32.

Primary Examiner—Ruth S. Smith
Attorney, Agent, or Firm—Quarles & Brady

[57] ABSTRACT

A magnetic resonance imaging system has a electromagnet coil assembly for exciting nuclei of an animal placed within the assembly and a mechanism to receive magnetic resonance signals from the nuclei and reconstruct an image of the animal from those signals. A plethysmograph is provided to sense the peripheral arterial pulse of the animal and gate the MRI system. A sensor for the plethysmograph includes a fiber optic cable having a pair of optical fibers which extend into the magnet assembly. A probe is connected to one end of the cable and is adapted to be attached to a digit of the animal so that ends of the optical fibers are adjacent the animal's skin. The other end of the cable couples to a circuit which sends light through one of the optical fibers to the probe, and which receives light returned from the probe through the other optical fiber. The circuit produces an electrical signal corresponding to the intensity of light received from the other optical fiber.

11 Claims, 5 Drawing Sheets

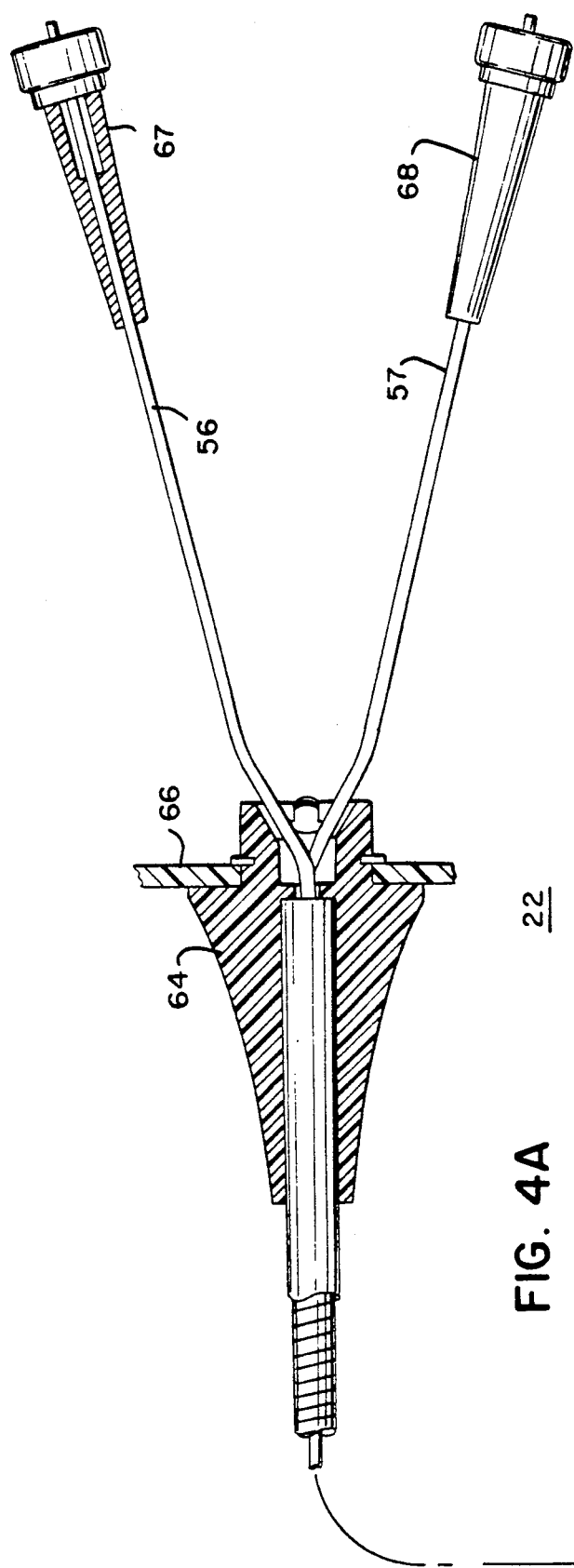
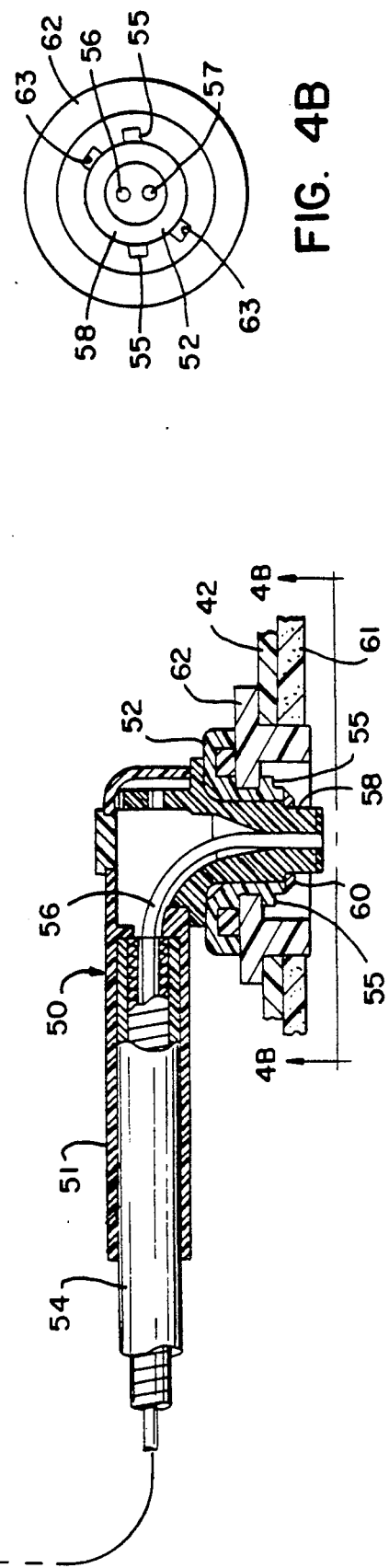
FIG. 4A
FIG. 4B

FIBER OPTIC PHOTOPLETHYSMOGRAPH FOR A MAGNETIC RESONANCE IMAGING SYSTEM

BACKGROUND OF THE INVENTION

The present invention relates to devices for detecting cardiac activity which utilize a plethysmograph; and more particularly to such devices for sensing the pulse from a patient during magnetic resonance imaging.

Magnetic resonance has been developed as an imaging method useful in diagnostic medicine. In magnetic resonance imaging (MRI) as is understood by those skilled in the art, a body being imaged is held within a uniform magnetic field oriented along a Z axis of a Cartesian coordinate system.

The net magnetizations of the nuclei in the body are excited to precession by means of a radio frequency (RF) pulse and the decaying precession of the spins produces the MRI signal. The amplitude of the MRI signal is dependent, among other factors, on the number of precession nuclei per volume within the image body termed the "spin density."

Magnetic gradient fields $G_x$, $G_y$ and $G_z$ are applied along the X, Y and Z axes to impress position information onto the MRI signals through phase and frequency encoding. A set of MRI signals may then be "reconstructed" to produce an image. Each set of MRI signals is comprised of many "views," a view being defined as one or more MRI signal acquisitions made under the same X and Y gradient fields.

The length of time needed to acquire a sufficient number of views to reconstruct an image may be on the order of several minutes. Therefore, motion of the subject, including cardiac and respiratory motion, is inevitable. Such motion may produce blurring of the image or other image artifacts depending on the image reconstruction technique used. Two common image reconstruction techniques are associated with "spin warp" imaging as described in U.S. Pat. No. 5,051,903 or multiple angle projection reconstruction as disclosed in U.S. Pat. No. 4,471,306.

Object motion during the acquisition of an MRI image produces both blurring and "ghosts" in the phase encoded direction. Ghosts are particularly apparent when the motion is periodic, or nearly so. Both blurring and ghosts can be reduced if the data acquisition is synchronized with the functional cycle of the object. This method is known as gated MRI scanning, and its objective is to acquire MRI data at the same point during successive functional cycles so that the object "looks" the same in each view. Other techniques have been devised for removing the artifacts from the acquired data. For example, U.S. Pat. Nos. 4,580,219; 4,663,591 and 4,706,026 disclose methods by which a signal indicative of the functional cycle of the object can be used to process the image data to reduce the blurring and ghosting effects.

One of the periodic physiological functions that affects the MRI image is the cardiac cycle. Conventional sensors for an electrocardiograph or an arterial pulse plethysmograph cannot be utilized with MRI equipment. As noted, very intense magnetic fields are applied to the patient, some of which vary at radio frequencies. These electromagnetic fields can induce large electric currents in conventional electrocardiograph or plethysmograph sensors and cables, thereby subjecting the patient to electrical shock or burn hazards during the MRI scan. Therefore, the equipment to sense the periodic physiological functions of a patient undergoing an MRI scan must be specially designed to withstand the magnetic resonance environment and provide adequate patient safety even in the presence of large gradient magnetic and radio frequency fields. In addition, the MRI operator must pay careful attention to how the physiological sensing equipment is set up and where the patient interface cables are placed within the bore of the MRI magnet.

Even with proper protective measures in place, the resulting signal from the sensor often contains large noise spikes caused by the varying magnetic fields. The noise spikes may be in the same frequency band as the physiological signal and are difficult to filter out of the data. In addition, the cables and sensor are visible in the magnetic resonance image.

SUMMARY OF THE INVENTION

A magnetic resonance imaging system has an electromagnet coil assembly for exciting nuclei of an animal placed within the assembly. The system includes means for sensing magnetic resonance signals emitted from the excited nuclei and using the sensed information to reconstruct an image of the animal.

A plethysmograph is provided to produce an electrical signal representing the arterial pulse of the animal for use in gating the operation of the magnetic resonance imaging system. The plethysmograph has a fiber optic cable with first and second optical fibers. One end of the cable is connected to a probe that is attached to the animal. One embodiment of the probe has a body with two sections, each having an elongated concave shape and being pivotally connected to the other section at one end. One of the sections has pawl fingers at another end which releasably engage a teeth in the other section. In a closed state, the two sections form an opening for receiving a digit of the animal. The probe and the fiber optical cable are fabricated from non-metallic, non-electrical conductive materials.

A connector is located at one end of the fiber optic cable for attaching to the probe so that ends of the first and second optical fibers are adjacent the skin of the animal. The other end of the fiber optic cable has a means for connecting the first optical fiber to a light source, and a means for connecting the second optical fiber to a receiver that produces an electrical signal which varies in response to light received from the optical fiber.

A purpose of the present invention is to provide a sensor for a plethysmograph to detect the peripheral arterial pulse of an animal being examined by a magnetic resonance imaging system.

Another object is to provide non-metallic, non-electrical conductive components of the portion of the sensor that are to extend into the magnet assembly. The use of such materials eliminates the hazard of shocks or burns to the patient which could result from interaction of the intense radio frequency electromagnetic fields with metallic and electrical conductive components. In addition, the sensor using the preferred materials will not be visible in the magnetic resonance image.

A further object of the present invention is to provide a medium for transmitting physiological information from within the magnet assembly which is immune from electrical noise due to the intense radio frequency electromagnetic fields.

BRIEF DESCRIPTION OF THE DRAWINGS

FIGS. 4A and 4B illustrate a fiber optic cable that connects the finger probe to electro-optic circuitry;

DESCRIPTION OF THE PRESENT INVENTION

Figure 1:
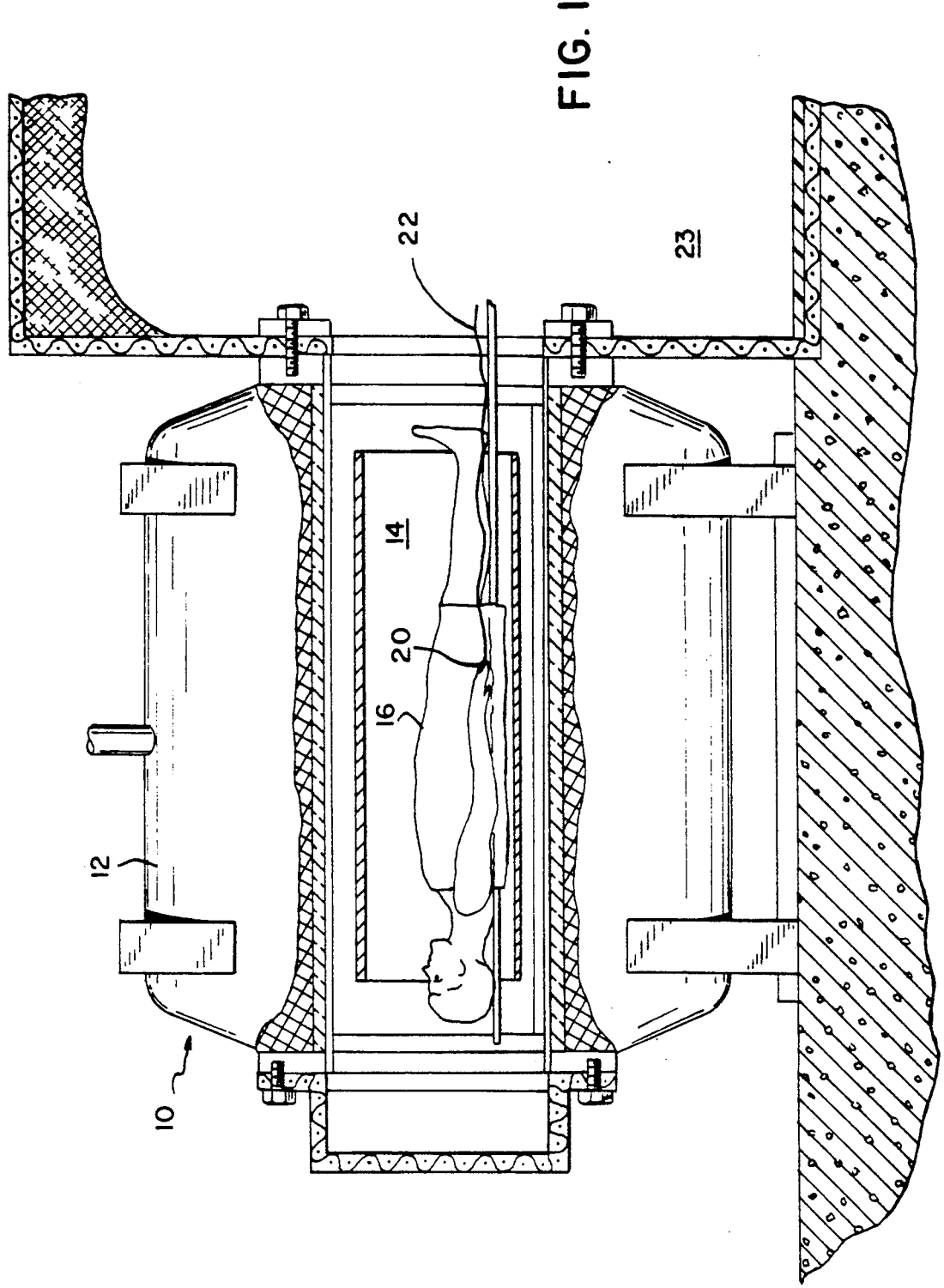
FIG. 1 is a partial cross-sectional view of electromagnet assembly for an MRI system utilizing the present invention.

With initial reference to FIG. 1, an MRI system 10 includes a magnet assembly 12 formed by a plurality of super conducting electromagnet coils enclosed in a conventional hollow, cylindrical cryostat chamber. The magnet assembly 12 has a generally cylindrical shape about a longitudinal axis defining an interior volume 14 within which a medical patient 16, for example, is placed for imaging.

A photoplethysmograph probe 20 is attached to a finger of the patient 16. A fiber optic cable 22 extends from the probe 20 through the magnet assembly 12 to a plethysmograph located in a shielded area 23 with the electronic equipment which controls the MRI system 10.

Figure 2:
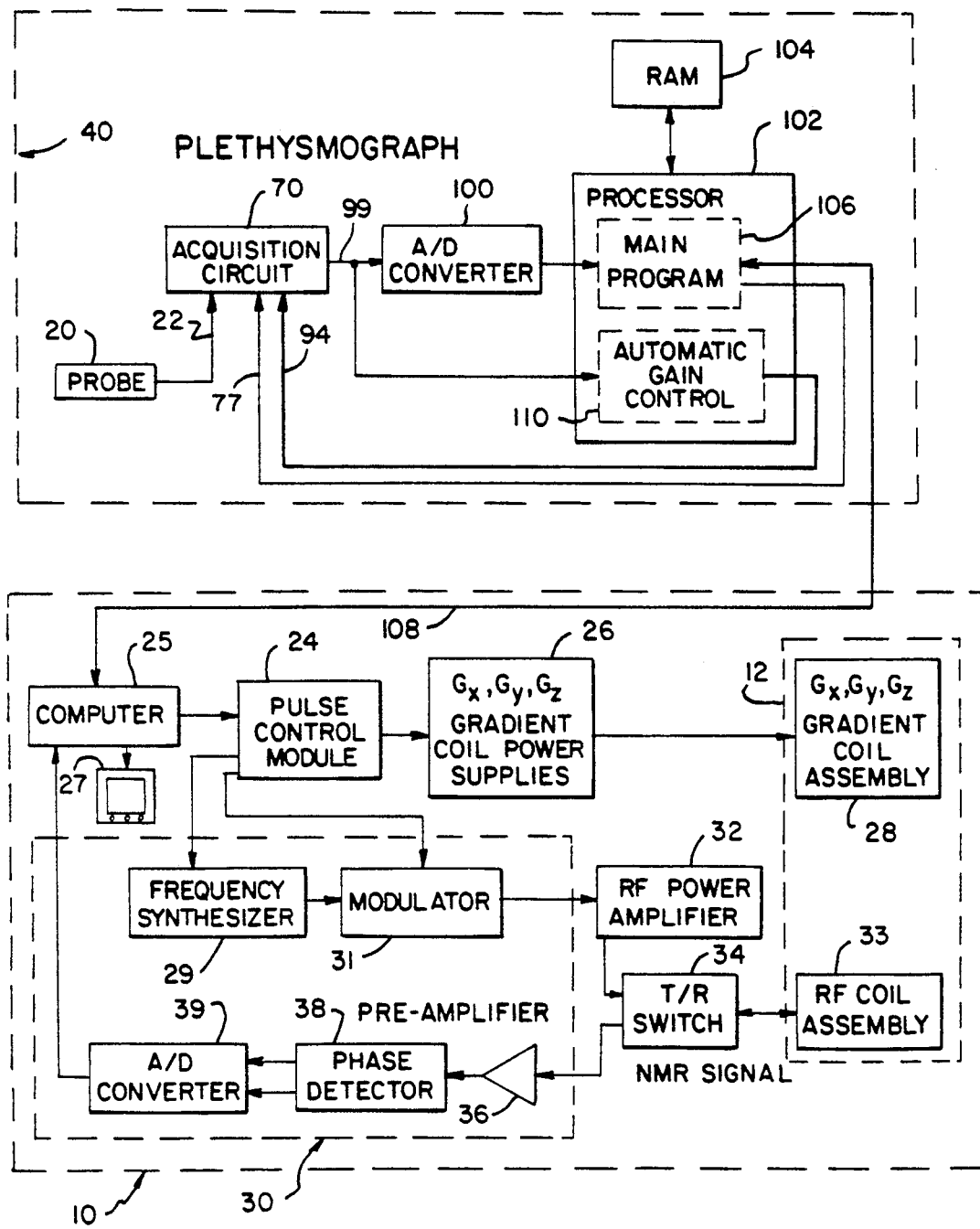
FIG. 2 is a block diagram of an exemplary MRI system incorporating a plethysmograph.

The control circuitry for the MRI system 10 is shown in FIG. 2, and includes a pulse control module 24 which provides conventional, properly-timed pulse sequences under the control of a computer 25. The pulse control module 24, in turn, governs gradient power supplies 26 which produce the magnetic field gradients $G_x$, $G_y$ and $G_z$ by means of gradient coils 28 within assembly 12.

The pulse control module 24 also controls a radio frequency synthesizer 29 which is part of an RF transceiver system, portions of which are enclosed by dashed line block 30. The pulse control module 24 also controls an RF modulator 31. The resultant RF signal is amplified by a power amplifier 32 and applied to an RF coil 33 assembly in assembly 12 through transmit/receive switch 34. These RF signals are used to excite the spinning of nuclei in the patient 16.

The magnetic resonance signals from the excited nuclei are picked up by RF coil assembly 33 and applied to preamplifier 36 through transmit/receive switch 34. The output of the preamplifier 36 is coupled to the input of a quadrature phase detector 38. The detected signals are digitized by a high speed analog-to-digital (A/D) converter 39 and are applied to computer 25 for processing to produce MRI images of the patient on display 27.

Figure 3:
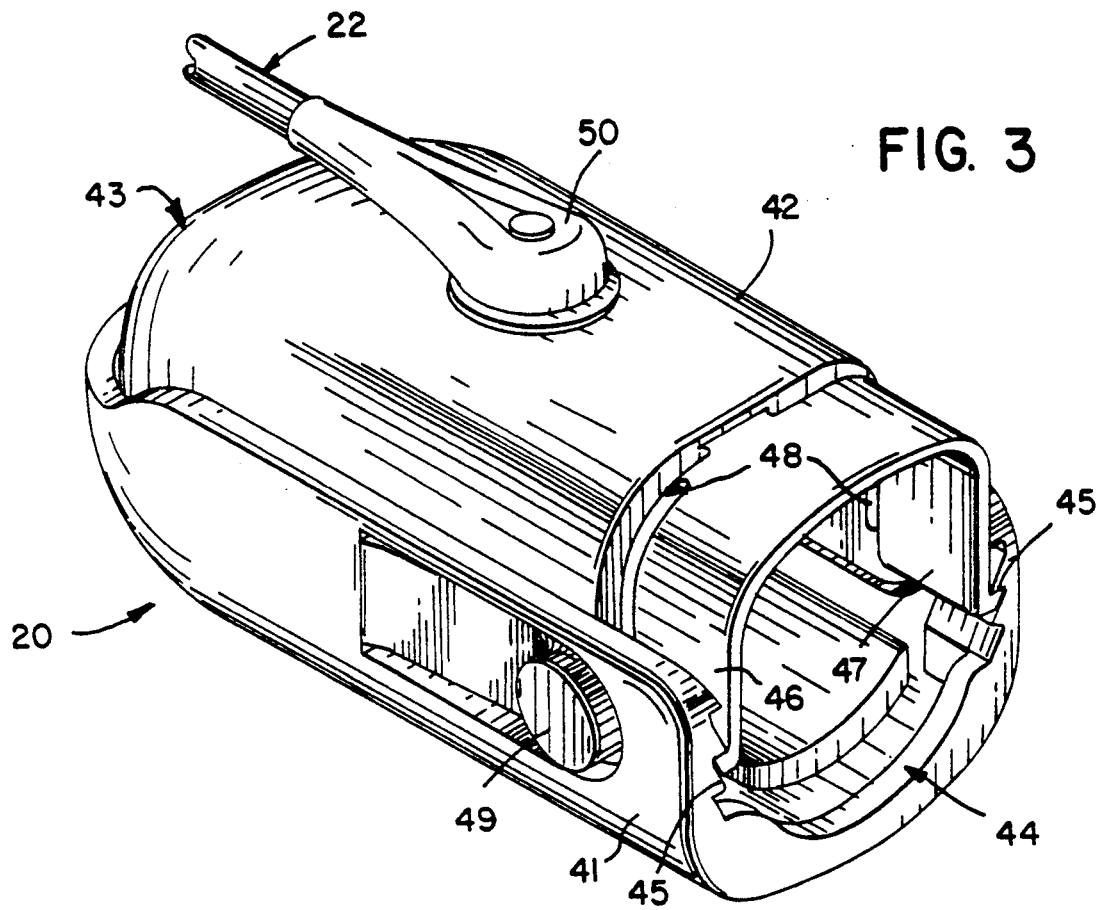
FIG. 3 is a isometric view of a finger probe for sensing the arterial pulse of a patient within the magnet assembly in FIG. 1.

The plethysmograph 40 for the MRI system 10 includes the probe 20 for sensing the arterial pulse of the patient 16. With reference to FIG. 3, the probe 20 has a base 41 and a cover 42 hinged together adjacent one end 43 to open like a clam shell. The base 41 and cover 42 are concave elements having open ends which form an opening 44 at the other end of the probe to receive the patient's finger. The probe 20 is shown in the closed state in which pawl fingers 46 and 47 at the other end of the cover 42 engage teeth 45 on the inside surface of the base 41. The pawl fingers 46 and 47 are separated by grooves 48 from the main portion of the cover 42 allowing the fingers to flex. Push levers 49 are located in opposite sides of the base 41. When the push levers 49 are squeezed together between opposing fingers of an MRI technician, the levers push the pawl fingers 46 and 47 inward releasing the pawls from engagement with the teeth 45 allowing the cover and base to be separated.

When the probe 20 is to be placed on a finger of the patient, the base and cover are opened and the finger is inserted within the base. The cover 42 then is closed until the pawl fingers 46 and 47 engage the teeth 45 to provide a secure fit of the probe onto the patient's finger. Resilient pads (not shown) are attached to the inside surfaces of both the base 41 and the cover 42 to cushion the patient's finger when the probe is in place.

An aperture is centrally located through the probe cover 42. A connector 50 at one end of the fiber optic cable 22 attaches to the probe 20 through the aperture in the cover 42. The probe provides a mechanism which holds an end of the fiber optic cable 22 against the skin of the patient in order to sense the patient's arterial pulse.

With reference to FIGS. 4A and 4B, the cable connector 50 has a main body 51 attached to an end of the optical fiber bundle 54 of cable 22. A cylindrical, tubular portion 58 of the connector 50 extends at a right angle from the main body 51. The fiber bundle 54 has two optical fibers 56 and 57, which bend 90 degrees within the connector 50 exiting through an opening in the exposed end of portion 58. Ends of the optical fibers 56 and 57 project for a small amount from connector portion 58. The optical fibers are either glass or a plastic that is highly transmissive to the light wavelengths being employed. Alternatively, two small bundles of optical fibers may be substituted for individual fibers 56 and 57.

Connector portion 58 passes through the aperture in probe cover 42 and a locking sleeve 52 is held in place around the portion by a retainer ring 60 in a manner which allows rotation of the locking sleeve. Part of the locking sleeve 52 passes through a collar 62 that is adhesively attached to the cover 42. The collar 62 extends through the aperture in the probe cover 42 and an aperture in a resilient pad 61 attached to the inner surface of the cover. The locking sleeve 52 has tabs 55 which pass through holes 63 in the collar 62 providing a bayonet-type locking mechanism for attaching the cable connector 50 to the probe 20. The swivel coupling of the locking sleeve 52 and the connector portion 58 allows the connector 50 to swivel while attached to the probe 20. The swivel action provides flexibility in positioning the probe and the hand of the patient within the MRI system.

Figure 5:
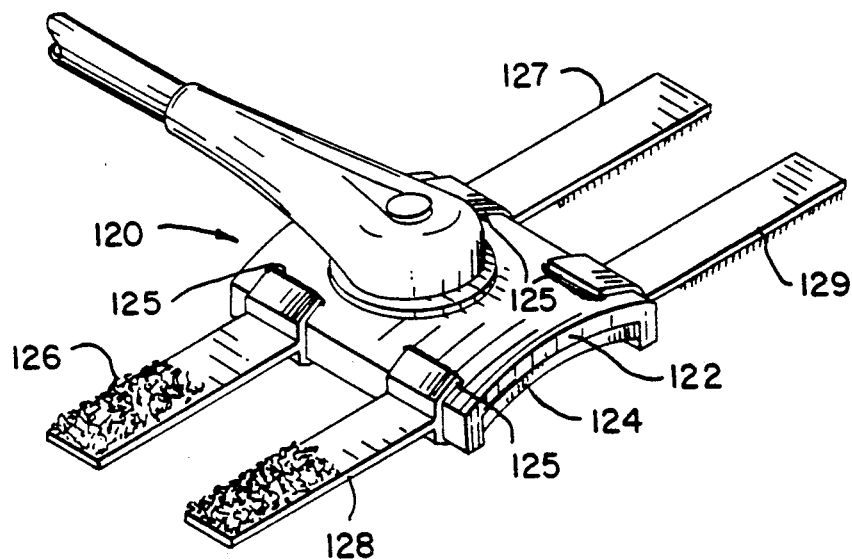
FIG. 5 is an isometric view of another probe for a different part of the patient's body.

FIG. 5 illustrates an alternative device 120 for attaching the end of the fiber optic cable 22 to the patient. This device includes a curved shell 122 having a pad 124 of resilient material attached to its concave surface. Pairs of slots 125 are located along opposite edges of the shell 122 with a separate strap 126, 127, 128 or 129 attached by a closed loop therethrough. The straps are formed of hook and loop fastening material. Alternatively, the four separate straps 126-129 could be replaced by two straps which pass through two opposed slots 125 in the shell 122. The shell is adapted to be placed against a toe of the patient with opposing straps wrapped around the toe and connected together. The shell 122 has an aperture through which the connector 50 of the fiber optic cable 22 attaches in a manner similar to that used with probe 20.

Both probe 20 and device 120 are fabricated entirely from non-metallic, non-electrically conductive materials, such as plastics. Likewise, the fiber optic cable 22 also is made from non-metallic, non-electrically conductive components. The same holds true for other types of attachment mechanisms that can be used to hold one end of the optical fibers 56 and 57 against the patient's skin to sense the arterial pulse. As components of the present plethysmograph 40 that are placed inside the magnet assembly 12 are made from non-metallic, non-conductive materials, the hazard of the patient being subjected to electrical shock or burning from the intense electromagnetic fields interacting with metallic components is eliminated.

The end of the optical fiber bundle 54 remote from connector 50 terminates at a resilient strain relief 64 located in an opening through a cabinet 66 for the plethysmograph 40. The two optical fibers 56 and 57 extend from the strain relief 64 terminating in separate connectors 67 and 68, respectively. As shown in FIG. 2, the fiber optic connectors 67 and 68 connect to an acquisition circuit 70.

Figure 6:
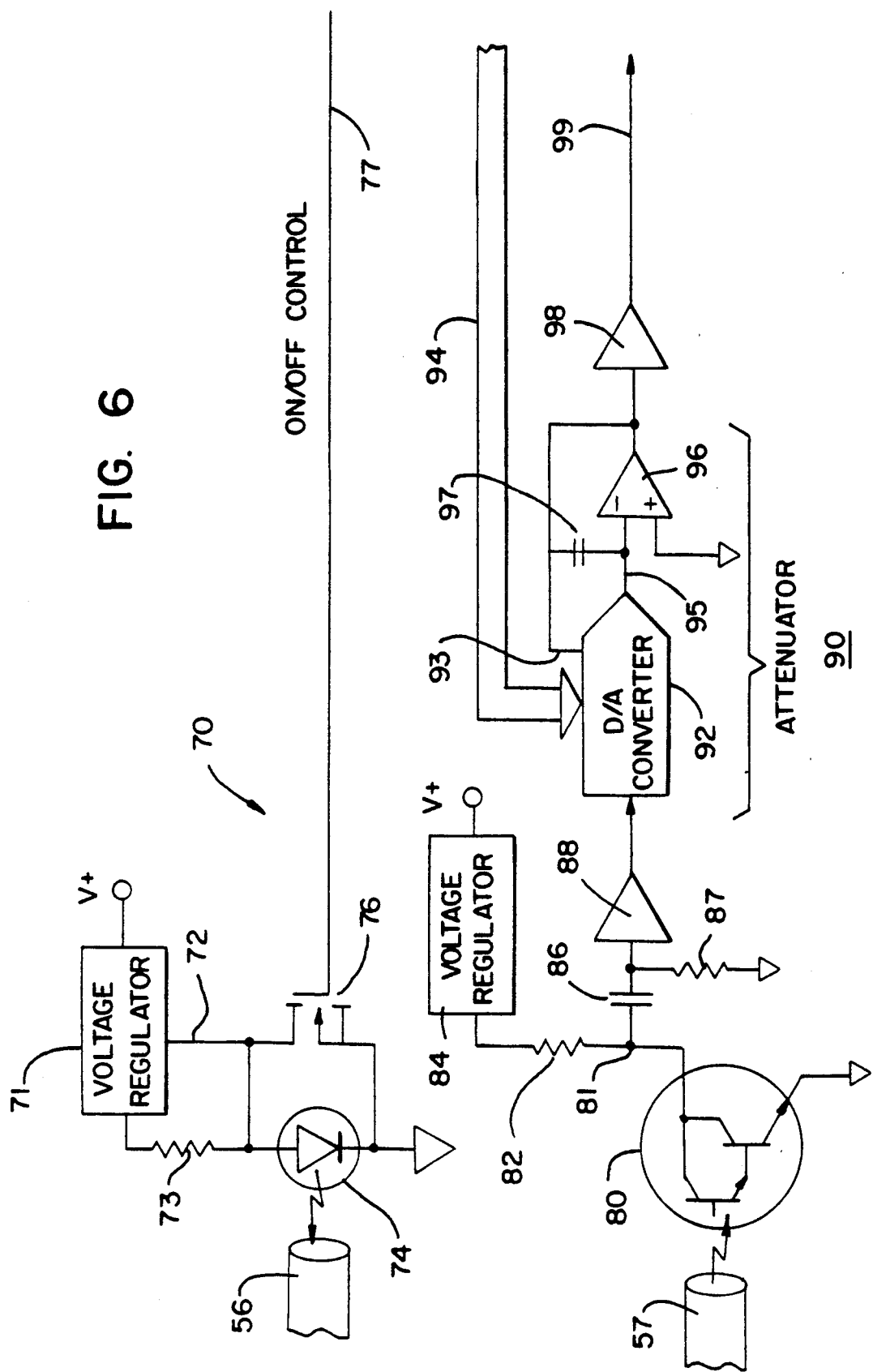
FIG. 6 is a schematic diagram of the electro-optic circuitry associated with the fiber optic cable and probe.

Referring to FIG. 6, the acquisition circuit comprises a section which generates light that is transmitted through the first optical fiber 56 to the probe, and another section which receives light from the probe via the second optical fiber 57 and converts that light into an electrical signal. The first section of the acquisition circuit 70 includes an adjustable voltage regulator 71 configured as a constant current source which responds to a control signal at input 72 by producing a regulated output current. The output of voltage regulator 71 is coupled by resistor 73 to the anode of an infrared light emitting diode (LED) 74 having its cathode connected to ground. The conduction path of a field effect transistor 76 is connected in parallel across the LED 74 and also couples the regulating input 72 of the voltage regulator 71 to ground. The gate of the field effect transistor 76 receives an ON/OFF control signal via line 77 which selectively turns on the LED 74. The light emitted by the LED 74 is optically coupled to the first optical fiber 56, thereby sending the light to probe 22.

The light is emitted from the probe end of the first optical fiber 56 and impinges upon the skin of the patient's finger within the probe 20. The light entering the finger is scattered and reflected by tissue and blood in the finger and varies with the pulsating blood flow. As a result, the amount of light scattered and reflected by the patient's finger into the second optical fiber 57 varies with the arterial pulse of the patient. The light entering the second optical fiber 57 is conducted to the data acquisition circuit 70.

At the acquisition circuit 70, the end of second optical fiber 57 is optically coupled to a Darlington phototransistor 80 that is responsive to the infrared wavelength emitted by LED 74. The conduction path of the phototransistor 80 is connected between ground and node 81. Resistor 82 connects node 81 to the output of a second voltage regulator 84. Therefore, the instantaneous voltage level at node 81 depends upon the conductivity of phototransistor 80 which varies in response to the light received from the second optical fiber 57. This light in turn varies with the arterial pulse of the patient.

Node 81 is coupled by capacitor 86 to the input of a first amplifier 88 whose input is coupled to ground by resistor 87. The combination of capacitor 86 and resistor 87 provides a high pass filter. The first amplifier 88 has an internal low pass filter to block signals above 25 Hertz. The output of the first amplifier 88 is connected to the input of a digitally controlled attenuator 90.

The attenuator 90 comprises a multiplying digital-to-analog (D/A) converter utilizing an "inverted R-2R" ladder structure, such as model AD 7541A manufactured by Analog Devices Inc. The output of amplifier 88 is applied at a voltage reference terminal of the D/A converter. The output from the digital-to-analog converter 92 at terminal 95 is dependent upon the level of the input voltage from amplifier 88, a digital scaling value received from parallel data bus 94, and a feedback voltage applied at terminal 93. By applying different scaling values via bus 94, the output voltage can be attenuated by different factors.

The output terminal 95 of the D/A converter 92 is connected to the inverting input of an amplifier 96 within the attenuator 90. The output of the amplifier 96 is connected directly to the feedback input terminal 93 of the D/A converter 92, and by capacitor 97 to the inverting input of the amplifier. The output of the amplifier 96 within the attenuator 90 is connected to the input of a fixed gain amplifier 98 to produce an output signal from the acquisition circuit 70 on line 99 which represents the arterial pulse of the patient.

Referring again to FIG. 2, output line 99 from acquisition circuit 70 is connected to the input of an analog-to-digital (A/D) converter 100 which provides a digitized representation of the pulse signal to a processor 102 within the plethysmograph 40. The processor 102 stores certain values of the pulse signal in a data base within random access memory (RAM) 104 which are used by a main program 106 to determine when to issue a gating signal via lines 108 to the computer 25 of the MRI system 10. The main program 106 is similar to those employed in previous plethysmographs for MRI systems.

The main control program 106 also responds to a signal from the MRI system computer 25 by issuing the ON/OFF control signal via line 77 to the acquisition circuit 70.

The processor 102 additionally computes a scaling value for the digital-to-analog converter 92 within the acquisition circuit 70. This scaling value is computed by an automatic gain control 110 which receives the output signal on line 99 from the acquisition circuit 70. The automatic gain control 110 compares the output signal to a pair of reference levels to determine whether the attenuation provided by circuit 90 in FIG. 6 should be increased or decreased. The result of the comparison controls counters within the automatic gain control 10 which produce the digital scaling value on bus 94. This gain control insures that the patient's pulse signal on line 99 will correspond to the full dynamic range of A/D converter 100.

The present plethysmograph design offers several advantages over previous devices. The components of the probe 20 and fiber optic cable 22 that are placed inside the magnet assembly 12 are made from non-metallic, non-conductive material. This eliminates hazard of the patient being subjected to electrical shocks or burns from the intense electromagnetic fields interacting with metallic components. Further the use of an optical signal to carry physiological information out of the magnet assembly renders the signal immune from electrical noise due to the radio frequency fields. The electronic and metallic components of the plethysmograph are located remote from the magnet assembly 12 and are shielded from the intense fields produced by that assembly.

The invention being claimed is:

1. A sensor for a plethysmograph which senses a physiological phenomenon in an animal, said sensor comprising:
   a fiber optic cable having first and second optical fibers, and having one end at which both of the first and second optical fibers are exposed;
   a body formed by first and second sections, each section having an elongated concave shape and being pivotally connected to the other section adjacent to one end, the first section having a pawl finger which releasably engages a tooth of the second section, the first and second sections having openings for receiving a digit of the animal, and one of the sections having an aperture;
   a connector attached to the one end of said fiber optic cable and passing through the aperture in the one section to hold both the first and second optical fibers adjacent to one side of the digit of the animal; and
   a means for coupling the other end of the first and second optical fibers to the plethysmograph.

2. The sensor as recited in claim 1 wherein said connector comprises a first portion attached to the one end of said fiber optic cable; a second portion projecting substantially perpendicular from the first portion, with the first and second optical fibers passing through both portions and through an end of the second portion; and means for releasably connecting said second portion to said body.

3. The sensor as recited in claim 1 wherein the first section of said body further includes a lever that engages the pawl fingers to release the pawl finger from engagement with the tooth.

4. In a magnetic resonance imaging system having a electromagnet coil assembly for exciting nuclei in an animal placed within the assembly, a plethysmograph comprising:
   a fiber optic cable having first and second optical fibers, and having one end at which both of the first and second optical fibers are exposed;
   a body curved to conform to a surface of an anatomical member of the animal, and having means for receiving the one end of said fiber optic cable to hold both the first and second optical fibers adjacent to one side of the anatomical member, and including a means for fastening said body around the anatomical member;
   a connector having a first portion attached to the one end of said fiber optic cable, and a second portion projecting substantially perpendicular from the first portion, with the first and second optical fibers extending through both portions and through an aperture in an end of the second portion, the second portion being rotatably connected to said body;
   a means, coupled to the other end of said fiber optic cable outside the electromagnet coil assembly, for generating light which is coupled to the first optical fiber; and
   a means, coupled to the other end of said fiber optic cable outside the electromagnet coil assembly, for producing an electrical signal which varies in response to light received from the second optical fiber.

5. The plethysmograph as recited in claim 4 wherein said body comprises a base and a cover hinged to one another, and having a opening adapted to receive a digit of the animal.

6. The plethysmograph as recited in claim 4 wherein said body comprises first and second sections, each section having an elongated concave shape and being pivotally connected to the other section adjacent one end, the first section having pawl fingers at another end which releasably engage teeth at another end of said second section, said first and second sections having openings for receiving a digit of the animal and one of said sections having an aperture which receives the one end of said fiber optic cable.

7. The plethysmograph as recited in claim 4 wherein said body has two opposite edges, and said means for fastening comprises a first strap attached to said member adjacent one edge, and a second strap attached to said member adjacent the other edge.

8. The plethysmograph as recited in claim 4, wherein a said connector being removably connected to said body.

9. The plethysmograph as recited in claim 4 wherein said means for generating light comprises an infrared light emitting diode.

10. The plethysmograph as recited in claim 4 wherein said means producing an electrical signal comprises:
   a light sensor optically coupled to an end of the second optical fiber and producing a electrical signal which corresponds to light received from the second optical fiber;
   means for amplifying the electrical signal from said sensor; and
   means for attenuating an output signal from said means for amplifying by an amount defined by an control signal.

11. The plethysmograph as recited in claim 10 further comprising an automatic gain control which produces the control signal for said means for attenuating in response to an output from said means for producing an electrical signal.

* * * * *